(12) United States Patent
deBettencourt, III et al.

(10) Patent No.: US 7,939,675 B2
(45) Date of Patent: May 10, 2011

(54) PROCESS FOR FORMING AMORPHOUS ATORVASTATIN

(75) Inventors: Antone John deBettencourt, III, Westerly, RI (US); Evgenyi Yur'evich Shalaev, Old Lyme, CT (US)

(73) Assignee: Pfizer, Inc., New York, NY (US)

( * ) Notice: Subject to any disclaimer, the term of this patent is extended or adjusted under 35 U.S.C. 154(b) by 675 days.

(21) Appl. No.: 11/666,707

(22) PCT Filed: Oct. 12, 2005

(86) PCT No.: PCT/IB2005/003173
§ 371 (c)(1),
(2), (4) Date: Mar. 12, 2008

(87) PCT Pub. No.: WO2006/046109
PCT Pub. Date: May 4, 2006

(65) Prior Publication Data
US 2008/0269314 A1 Oct. 30, 2008

Related U.S. Application Data

(60) Provisional application No. 60/623,086, filed on Oct. 28, 2004.

(51) Int. Cl.
*C07D 207/412* (2006.01)
(52) U.S. Cl. ..................................................... 548/537
(58) Field of Classification Search .................. None
See application file for complete search history.

(56) References Cited

U.S. PATENT DOCUMENTS

| | | | |
|---|---|---|---|
| 4,681,893 A | 7/1987 | Roth | 514/422 |
| 5,003,080 A | 3/1991 | Butler et al. | 548/517 |
| 5,097,045 A | 3/1992 | Butler et al. | 549/373 |
| 5,103,024 A | 4/1992 | Millar et al. | 549/373 |
| 5,124,482 A | 6/1992 | Butler et al. | 564/169 |
| 5,149,837 A | 9/1992 | Butler et al. | 549/333 |
| 5,155,251 A | 10/1992 | Butler et al. | 558/442 |
| 5,216,174 A | 6/1993 | Butler et al. | 548/517 |
| 5,245,047 A | 9/1993 | Butler et al. | 548/517 |
| 5,248,793 A | 9/1993 | Millar et al. | 549/375 |
| 5,273,995 A | 12/1993 | Roth | 514/223 |
| 5,280,126 A | 1/1994 | Butler et al. | 548/517 |
| 5,298,627 A | 3/1994 | Butler et al. | 548/517 |
| 5,342,952 A | 8/1994 | Butler et al. | 546/245 |
| 5,397,792 A | 3/1995 | Butler et al. | 514/326 |
| 5,446,054 A | 8/1995 | Butler et al. | 514/326 |
| 5,470,981 A | 11/1995 | Butler et al. | 546/207 |
| 5,489,690 A | 2/1996 | Butler et al. | 546/245 |
| 5,489,691 A | 2/1996 | Butler et al. | 548/517 |
| 5,510,488 A | 4/1996 | Butler et al. | 546/207 |
| 5,686,104 A | 11/1997 | Mills et al. | 424/451 |
| 5,969,156 A | 10/1999 | Briggs et al. | 548/537 |
| 5,998,633 A | 12/1999 | Jacks et al. | 549/313 |
| 6,087,511 A | 7/2000 | Lin et al. | 548/537 |
| 6,121,461 A | 9/2000 | McKenzie | 548/530 |
| 6,126,971 A | 10/2000 | Mills et al. | 424/484 |
| 6,274,740 B1 | 8/2001 | Lin et al. | 548/537 |
| 6,433,213 B1 | 8/2002 | Bosch et al. | 558/441 |
| 6,476,235 B2 | 11/2002 | Butler et al. | 548/517 |
| 6,528,660 B1 | 3/2003 | Kumar et al. | 548/537 |
| 6,598,010 B2 | 7/2003 | Zefira | 702/173 |
| 6,605,729 B1 | 8/2003 | Byrn et al. | 548/537 |
| 6,613,916 B2 | 9/2003 | Pflaum | 548/537 |
| 6,750,353 B2 | 6/2004 | Sorsak | 548/537 |
| 6,867,306 B2 | 3/2005 | Srinath et al. | 548/517 |
| 6,891,047 B2 | 5/2005 | Pflaum | 548/537 |
| 7,230,120 B2 | 6/2007 | Poornaprajan et al. | 548/537 |
| 2004/0186162 A1 | 9/2004 | Poornaprajna et al. | 514/423 |
| 2006/0122403 A1 | 6/2006 | Suri et al. | 548/537 |

FOREIGN PATENT DOCUMENTS

| | | |
|---|---|---|
| WO | WO0128999 | 4/2001 |
| WO | WO0136384 | 5/2001 |
| WO | WO 02/43732 | * 11/2001 |
| WO | WO0241834 | 5/2002 |
| WO | WO0243667 | 6/2002 |
| WO | WO0243732 | 6/2002 |
| WO | WO02051804 | 7/2002 |
| WO | WO02057228 | 7/2002 |
| WO | WO02057229 | 7/2002 |
| WO | WO02059087 | 8/2002 |
| WO | WO02083637 | 10/2002 |
| WO | WO02083638 | 10/2002 |
| WO | WO03007072 | 1/2003 |
| WO | WO03011826 | 2/2003 |
| WO | WO03050085 | 6/2003 |
| WO | WO2004022053 | 3/2004 |

OTHER PUBLICATIONS

Chawla et al., "Challenges in Polymorphism of Pharmaceuticals", CRIPS vol. 5, No. 1, Jan.-Mar. 2004 (4 Pages.*
Newman et al., "Solid-state analysis of the active pharmaceutical ingredient in drug products", DDT vol. 8, No. 19, Oct. 2003, p. 898-905.*
Konno, T., Physical and chemical changes of medicinal in mixtures with adsorbents in the solid state. IV. Study on reduced-pressure mixing for practical use of amorphous mixtures of flufenamic acid, *Chemical and Pharmaceutical Bulletin*, vol. 38, No. 7, pp. 2003-2007, (Jul. 1990).
Takemoto, M., et al., Statins as antioxidant therapy for preventing myocyte hypertrophy, *Journal of Clinical Investigation*, vol. 108, No. 10, pp. 1429-1437, (Nov. 2001).

* cited by examiner

*Primary Examiner* — Sun Jae Y Loewe
(74) *Attorney, Agent, or Firm* — Jennifer A. Kispert; Francis J. Tinney

(57) ABSTRACT

A process for forming amorphous atorvastatin comprising the steps of dissolving atorvastatin in a non-hydroxylic solvent and removing the solvent by freeze-drying, as well as processes of dissolving atorvastatin in a hydroxylic solvent with a solubilizing agent or an alkalizing agent or an antioxidant and removing the solvent by freeze-drying to afford amorphous atorvastatin.

3 Claims, 5 Drawing Sheets

PROCESS FOR FORMING AMORPHOUS ATORVASTATIN

CROSS REFERENCE

This application claims benefit of U.S. Provisional Patent Application No. 60/623,086, filed Oct. 28, 2004.

FIELD OF THE INVENTION

The invention relates to processes for forming amorphous atorvastatin by lyophilization of atorvastatin from a solution.

BACKGROUND OF THE INVENTION

The conversion of 3-hydroxy-3-methylglutaryl-coenzyme A (HMG-CoA) to mevalonate is an early and rate-limiting step in the choloesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin calcium is currently sold as Lipitor® having the chemical name [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate and the formula

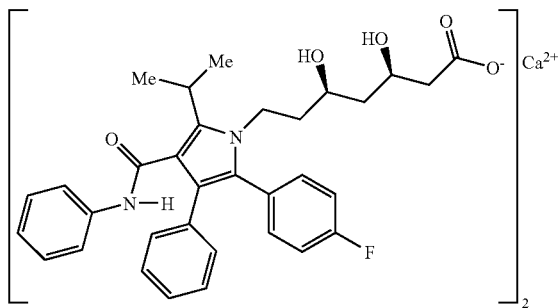

Atorvastatin and pharmaceutically acceptable salts thereof are selective, competitive inhibitors of HMG-CoA reductase. As such, atorvastatin calcium is a potent lipid lowering compound and is thus useful as a hypolipidemic and/or hypocholesterolemic agent, as well as in the treatment of osteoporosis, benign prostatic hyperplasia (BPH) and Alzheimer's disease.

A number of patents have issued disclosing atorvastatin, formulations of atorvastatin, as well as processes and key intermediates for preparing atorvastatin. These include: U.S. Pat. Nos. 4,681,893; 5,273,995; 5,003,080; 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,686,104; 5,998,633; 6,087,511; 6,126,971; 6,433,213; and 6,476,235, which are herein incorporated by reference.

Additionally, a number of published International Patent Applications and patents have disclosed crystalline forms of atorvastatin, as well as processes for preparing amorphous atorvastatin. These include: U.S. Pat. Nos. 5,969,156; 6,121,461; 6,605,729; WO 01/36384; WO 02/41834; WO 02/43667; WO 02/43732; WO 02/051804; WO 02/057228; WO 02/057229; WO 02/057274; WO 02/059087; WO 02/083637; WO 02/083638; WO 03/011826; WO 03/050085; WO 03/07072; and WO 04/022053.

It has been disclosed that the amorphous forms of a number of drugs exhibit different dissolution characteristics and in some cases different bioavailability patterns compared to the crystalline form (Konno T., Chem. Pharm. Bull., 1990; 38:2003-2007). For some therapeutic indications one bioavailability pattern may be favored over another.

Variations in dissolution rates can make it advantageous to produce atorvastatin formulations in either crystalline or amorphous forms. For example, for some potential uses of atorvastatin (e.g., acute treatment of patients having strokes as described in Takemoto, M.; Node, K.; Nakagami, H.; Liao, Y.; Grimm, M.; Takemoto, Y.; Kitakaze, M.; Liao, J. K., Journal of Clinical Investigation, 2001; 108(10): 1429-1437) a rapid onset of activity may be highly beneficial in improving the efficacy of atorvastatin.

The preparation of amorphous atorvastatin has been previously disclosed. For example, Lin et al., U.S. Pat. No. 6,087,511 disclose forming amorphous atorvastatin from crystalline atorvastatin. To form amorphous atorvastatin, Lin et al. disclose that crystalline atorvastatin is dissolved in a non-hydroxylic solvent such as tetrahydrofuran. The non-hydroxylic solvent is removed to produce a brittle foam that is broken up by mechanical agitation to afford amorphous atorvastatin.

WO 00/71116 also discloses forming amorphous atorvastatin using a non-hydroxylic solvent.

WO 01/28999 discloses a process for forming amorphous atorvastatin by recrystallization of crude atorvastatin from an organic solvent which comprises dissolving crude amorphous atorvastatin calcium in a lower alkanol containing 2-4 carbon atoms or a mixture of such alkanols under heating. The amorphous atorvastatin calcium is precipitated after cooling.

WO 01/42209 discloses preparing amorphous atorvastatin by precipitating the atorvastatin using a solvent in which atorvastatin is insoluble or very slightly soluble, from a solution of atorvastatin which is provided with a solvent in which atorvastatin is freely soluble. Preferred solvents in which atorvastatin is freely soluble include low molecular weight alcohols, e.g. methanol and ethanol.

WO 03/078379 discloses forming amorphous atorvastatin by dissolving atorvastatin in a hydroxylic solvent and removing the solvent by either freeze-drying or spray drying.

US Published Patent Application 2004/0024046 A1 discloses a process for forming amorphous atorvastatin by precipitating atorvastatin from a solution with a solvent in which atorvastatin is insoluble or very slightly soluble.

The current processes for production of amorphous atorvastatin involve solvents which are not optimal due to toxicity or environmental concerns. In addition, current processes are not optimal in terms of production capabilities and are not suitable for large scale synthesis. Therefore, there remains a continuing need for improved methods for preparation of amorphous atorvastatin.

SUMMARY OF THE INVENTION

A first aspect of the present invention is a process for forming atorvastatin in an amorphous or other disordered state comprising the steps of: (a) dissolving atorvastatin in a non-hydroxylic solvent to form a solution; and (b) lyophilizing the solution to afford said amorphous atorvastatin.

In a preferred method, the non-hydroxylic solvent is selected from the group consisting of: dimethyl sulfoxide (DMSO), tetrahydrofuran, N-methylpyrrolidone, N,N-dimethylacetamide, N,N-dimethylformamide and the like, anisole (methoxybenzene), cumene (isopropylbenzene) and the like, small chain esters, such as, methyl acetate, ethyl acetate, isopropyl acetate, and the like, and ketones such as acetone and methyl ethyl ketone, and the like, and mixtures thereof.

We have unexpectedly found that a non-hydroxylic solvent such as, for example, DMSO, has a number of advantages over hydroxylic solvents such as methanol and ethanol, for example, a higher solubility of atorvastatin calcium in the non-hydroxylic solvent and a higher melting point.

Optionally, the non-hydroxylic solvent may contain an excipient or other additives, such as a solubilizing agent; or an alkalizing agent; or an antioxidant or mixtures thereof.

"Other disordered state" refers to partially crystalline materials and crystalline mesophases or glassy forms with e.g. one- or two-dimensional translational order (lipid crystals), or orientational disorder (orientationally disordered crystals), or with conformational disorder (conformationally disordered crystals), or stoichiometric disorder e.g. variable hydration state. As used herein, the term "amorphous" includes those materials that may be present in some "other disordered state".

A second aspect of the present invention is a process for forming amorphous atorvastatin comprising:

a. dissolving atorvastatin in a hydroxylic solvent with a solubilizing agent; and b. lyophilizing the solution to afford said amorphous atorvastatin.

In a preferred method, the hydroxylic solvent is selected from the group consisting of: water, an alcohol, such as, for example, methanol, ethanol, and the like, and mixtures thereof. Optionally, the hydroxylic solvent may contain other additives, such as an alkalizing agent; or an antioxidant or mixtures thereof.

The solubilizing agent is selected from the group consisting of: a surfactant; a complexing agent; a co-solvent; a polymer; and mixtures thereof.

Preferably, the surfactant is selected from the group consisting of: polyoxyethylene fatty acid esters (polysorbates), such as, for example, polysorbate 61, polysorbate 65, polysorbate 80 (Tween 80), and the like, and surfactants with a melting temperature above room temperature such as, for example, triethyl citrate, docusate sodium, sodium lauryl sulfate, cetrimide, sorbitan fatty acid esters (sorbitan esters), including sorbitan monopalmitate, sorbitan monostearate, sorbitan tristearate, and the like.

Preferably, the complexing agent is a cyclodextrin selected from the group consisting of: alpha-cyclodextrin, beta-cyclodextrin, and gamma-cyclodextrin, as well as derivatives thereof.

Preferably, the co-solvent is selected from the group consisting of: either hydroxylic solvents such as, for example, methanol, ethanol, and non-hydroxylic solvents such as, for example, DMSO, tetrahydrofuran, N-methylpyrrolidone, N,N-dimethylacetamide, N,N-dimethylformamide and the like, small chain esters, such as, methyl acetate, ethyl acetate, and the like, and ketones such as acetone and methyl ethyl ketone, and the like.

Preferably, the polymer is selected from the group consisting of: poloxamer 124, poloxamer 188, poloxamer 237, poloxamer 338, poloxamer 407, and the like.

We have unexpectedly found that the use of a solubilizer allowed for the carrying out of the freeze-drying cycle at conventional freeze-drying conditions and significantly increased the atorvastatin calcium load in the solution that is freeze-dried. Thus, this increases the effectiveness of the process and ensures that the process is amenable to large scale manufacturing.

A third aspect of the present invention is a process for forming amorphous atorvastatin comprising:

a) dissolving atorvastatin in a hydroxylic solvent containing an alkalizing agent; and b) lyophilizing the solution to afford said amorphous atorvastatin.

In a preferred method, the hydroxylic solvent is selected from the group consisting of: water, an alcohol, such as, for example, methanol, ethanol and the like, and mixtures thereof. Optionally, the hydroxylic solvent may contain other additives, such as a solubilizing agent; or an antioxidant or mixtures thereof.

The alkalizing agent is selected from the group consisting of: an alkali metal salt; an alkali metal hydroxide; an alkaline earth metal salt; and alkaline earth metal hydroxide; an amino acid; and a volatile base.

Preferably, the alkalizing agent is selected from the group consisting of: an alkali metal carbonate; an alkali earth metal carbonate; an alkali metal bicarbonate; an alkaline earth metal bicarbonate; and alkali metal phosphate; an alkaline earth metal phosphate; and a sodium phosphate such as sodium phosphate monobasic, dibasic, and tribasic.

More preferably, the alkalizing agent is selected from the group consisting of: a sodium salt; a potassium salt; an aluminum salt; a magnesium salt; and a calcium salt.

Preferably, the volatile base is selected from the group consisting of: ammonium hydroxide; a tetraalkylammonium hydroxide; a secondary amine; a tertiary amine; and an aryl amine; and ammonium bicarbonate. The volatile base can sublime, or evaporate, or decompose during processing either partially or completely.

More preferably, the volatile base is selected from the group consisting of: diethanolamine and monoethanolamine.

Most preferably, the volatile base is selected from the group consisting of ammonium hydroxide; and tetrabutylammonium hydroxide.

A fourth aspect of the present invention is a process for forming amorphous atorvastatin comprising:

a) dissolving atorvastatin and an antioxidant in a hydroxylic solvent; and b) lyophilizing the solution to afford said amorphous atorvastatin.

In a preferred method, the hydroxylic solvent is selected from the group consisting of: water, an alcohol, such as, for example, methanol, ethanol, and the like, or mixtures thereof. Optionally, the hydroxylic solvent may contain other additives, such as a solubilizing agent; or an alkalizing agent or mixtures thereof.

The antioxidant is selected from the group consisting of a chelating agent; a free-radical scavenger; and an oxygen scavenger or a mixture thereof.

Preferably, the chelating agent is selected from the group consisting of: a citrate; and ethylenediaminetetraacetic acid.

Preferably, the free-radical scavenger is selected from the group consisting of: butylated hydroxyanisole (BHA), and butylated hydroxytoluene (BHT), alpha-tocopherol and the like.

Preferably, the oxygen scavenger is selected from the group consisting of: sodium ascorbate; and potassium ascorbate.

A fifth aspect of the present invention is a therapeutic package or kit suitable for commercial sale, comprising a container and a therapeutically effective amount of amorphous atorvastatin calcium.

A sixth aspect of the present invention is a method of using amorphous atorvastatin calcium to treat subjects suffering from hypercholesterolemia and/or hyperlipidemia, osteoporosis, benign prostatic hyperplasia (BPH) and Alzheimer's disease.

The foregoing and other objectives, features and advantages of the invention will be more readily understood upon consideration of the following detailed description of the invention.

DETAILED DESCRIPTION OF THE INVENTION

Figure 1:
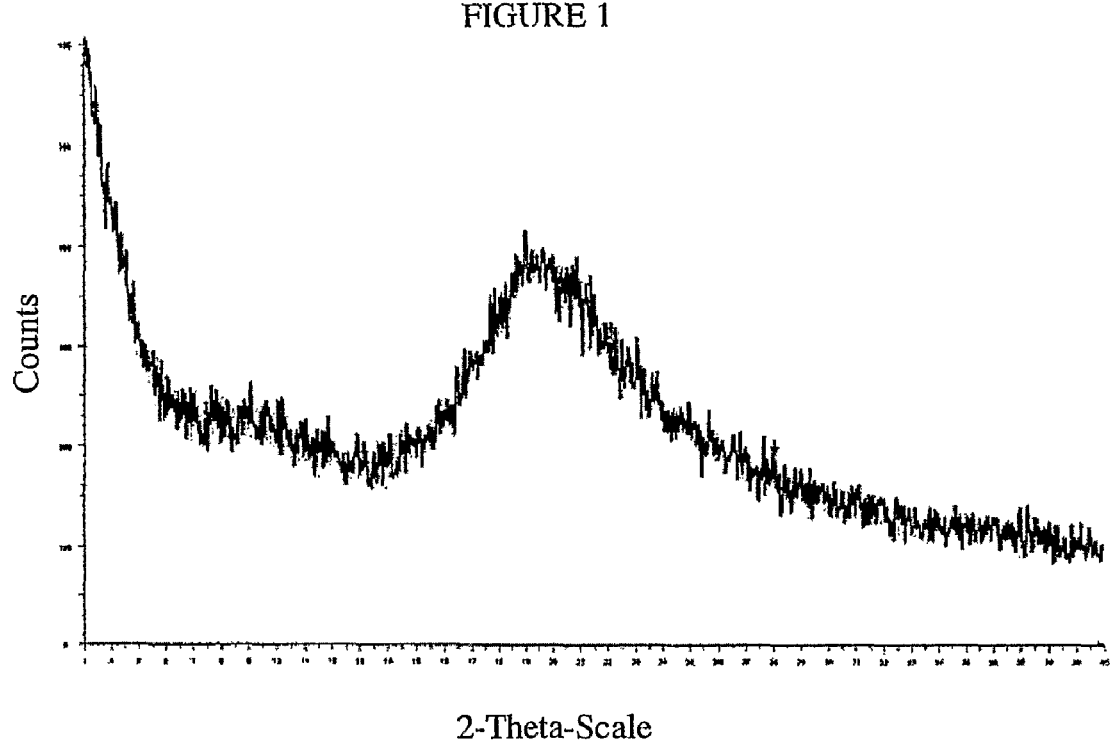
FIG. 1 shows a powder X-ray diffraction (XRD) diffractogram of amorphous atorvastatin calcium made in Example 1, Method A.

As will be recognized by those skilled in the art, the initial atorvastatin sample which is dissolved in a suitable solvent may be in any morphological form such as, for example, crystalline or amorphous, as well as disordered crystals, liquid crystals, plastic crystals, mesophases, glassy forms, and the like, or any combination thereof. Atorvastatin may readily be prepared, for example, as described in U.S. Pat. Nos. 4,681,893, 5,273,995, and 5,969,156 which are incorporated herein by reference. The term "atorvastatin" includes the free acid form, salt forms, solvates, hydrates and polymorphs. Pharmaceutically acceptable base addition salts of atorvastatin are formed with metals or amines, such as alkali and alkaline earth metal salts or organic amines. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts", J. of Pharm. Sci., 1977; 66:1).

A preferred form of atorvastatin is atorvastatin hemi-calcium salt trihydrate and sold under the tradename LIPITOR®.

The term "alkali metal" as used herein refers to a metal in Group IA of the periodic table and includes, for example, lithium, sodium, potassium and the like.

The term "alkaline-earth metal" as used herein refers to a metal in Group IIA of the periodic table and includes, for example, calcium, barium, strontium, magnesium, and the like.

The term "volatile base" as used herein refers to a base that can sublime, evaporate, or decompose during processing either partially or completely, such as, for example, ammonium hydroxide, a tetraalkylammonium hydroxide, such as, for example, tetraethylammonium hydroxide, tetrabutylammonium hydroxide and the like, a primary amine, such as, for example, monoethylamine, monoethanolamine, monopropylamino and the like, a secondary amine, such as, for example, dimethylamine, diethanolamine, diethylamine, dipropylamine, methylethylamine, and the like, a tertiary amine, such as, for example, aniline and the like, and benzalkonium chloride.

The term "hydroxylic solvent" as used herein refers to a solvent containing at least one hydroxyl group, such as, for example, water, methanol, ethanol, propanol, and the like.

The term "non-hydroxylic solvent" as used herein refers to a solvent which does not contain a hydroxyl group, such as, for example, DMSO, tetrahydrofuran, N-methylpyrrolidone, N,N-dimethylacetamide, N,N-dimethylformamide, an ester, such as, for example, methyl acetate, ethyl acetate, propylacetate, isobutylacetate, and the like, a ketone, such as, for example, acetone, methyl ethyl ketone and the like, methylbenzene, methoxybenzene (anisole), isopropylbenzene (cumene) and the like.

The term "amorphous atorvastatin or amorphous atorvastatin calcium" as used herein refers to different types of disordered forms including completely amorphous material, partially amorphous material, e.g., a mixture of crystalline and amorphous, and crystalline mesophases, e.g., liquid-crystal type structures.

The terms "lyophilization" or "lyophilizing" or "freeze-drying" are used interchangeably and refer to a process of freeze-drying a product under vacuum.

Amorphous material, and the amount of amorphous material present, may be characterized by techniques known in the art such as x-ray powder diffraction, solid state nuclear magnetic resonance (NMR) spectroscopy, or thermal techniques such as differential scanning calorimetry (DSC).

The present invention relates to the treatment of diseases and conditions in a subject, such as, hyperlipidemia and/or hypercholesterolemia, osteoporosis, benign prostatic hyperplasia (BPH) and Alzheimer's disease with amorphous atorvastatin calcium as described above that may be administered in a solid dosage form containing a pharmaceutically acceptable carrier or diluent and/or contained in a therapeutic package or kit. The kit may include the solid dosage form and a container. Typically, the kit includes directions for administration of the dosage form. The container can be in conventional shapes or forms, for example, plastic as described in U.S. Pat. No. 6,688,468 which is herein incorporated by reference or a glass container, or a blister pack with individual dosage for pressing out of the back according to the therapeutic schedule.

X-Ray Powder Diffraction (XRD)

The X-ray powder diffraction pattern of amorphous atorvastatin calcium was carried out on a Bruker D5000 diffractometer (Madison, Wis.) equipped with copper radiation (Cu $K_\alpha$). Data were collected from 3.0 to 40.0 degrees in two theta (2θ) using a step size of 0.04 degrees and a step time of 1.0 seconds. The divergence and scattering slits were set at 1 mm, and the receiving slit was set at 0.6 mm. Diffracted radiation was detected by a Kevex PSI detector. An alumina standard was analyzed to check the instrument alignment. Data were collected and analyzed using Bruker AXS software Version 7.0. Samples were prepared for analysis by placing them in a quartz holder with a cavity. It should be noted that Bruker Instruments purchased Siemans; thus, a Bruker D5000 instrument is essentially the same as a Siemans D5000.

$^{19}$F Solid State Nuclear Resonance ($^{19}$F SS NMR)

The solid-state nuclear magnetic resonance spectra of the amorphous forms of atorvastatin were carried out on a Bruker-Biospin Avance DSX 500 MHz NMR spectrometer. Approximately 15 mg of sample were tightly packed into a 2.5 mm ZrO spinner for each sample analyzed. One-dimensional $^{19}$F spectra were collected at 295 K and ambient pressure on a Bruker-Biospin 2.5 mm BL cross-polarization magic angle spinning (CPMAS) probe positioned into a wide-bore Bruker-Biospin Avance DSX 500 MHz NMR spectrometer. The samples were positioned at the magic angle and spun at 35.0 kHz with no cross-polarization from protons, corresponding to the maximum specified spinning speed for the 2.5 mm spinners. The fast spinning speed minimized the intensities of the spinning side bands and provided almost complete decoupling of $^{19}$F signals from protons. The number of scans were individually adjusted for each sample to obtain adequate single/noise (S/N). Typically, 150 scans were acquired. Prior to $^{19}$F acquisition, $^{19}$F relaxation times were measured by an inversion recovery technique. The recycle delay for each sample was then adjusted to five times the longest $^{19}$F relaxation time in the sample, which ensured acquisition of quantitative spectra. A fluorine probe background was subtracted in each alternate scan after presaturating the $^{19}$F signal. The spectra were referenced using an external sample of trifluoroacetic acid (diluted to 50% V/V by $H_2O$), setting its resonance to −76.54 ppm.

In the first aspect of the present invention, atorvastatin is dissolved in a non-hydroxylic solvent, such as, for example, DMSO and the like, or anisole (methoxybenzene), or cumen (isopropylbenzene), or isobutyl acetate, or a mixture thereof with other non-hydroxylic or hydroxylic solvent. Optionally, common pharmaceutical excipient(s) such as alkalizing agent(s), antioxidant(s), or solubilizer(s) may be added as needed. In general, primary drying (solvent sublimation) is performed at the product temperature below the melting point of the solvent, for example, 18.45° C. for DMSO, preferably above −40° C. Secondary drying is performed above the solvent melting point, usually below 60° C. The vacuum during primary and secondary drying is usually between about 5 and about 1000 mTorr, preferably between about 30 and about 200 mTorr. Time is determined by the type of equipment, container type (e.g., glass vials, stainless steel trays, and the like), amount of solvent to be removed and the sample configuration (e.g., sample thickness). Thus, the solution is loaded into vials and the vials loaded into a freeze-dryer, and the solution frozen to a shelf temperature of about −40° C. Lyophilization was started at a shelf temperature of about −24° C., followed by drying at a shelf temperature of about 0° C., and then about 5° C. Pressure was below about 50 m Torr during the drying cycle. The resulting amorphous atorvastatin was dried at about 40° C. for about 6 hours under vacuum in an oven, such as, for example, a vacuum oven.

Preferably, the starting atorvastatin is crystalline atorvastatin and the non-hydroxylic solvent is DMSO.

In the second aspect of the present invention, atorvastatin is dissolved in a hydroxylic solvent such as, for example, water and optionally buffered with a buffering agent, such as, for example, Dulbecco's phosphate buffered saline solution containing a solubilizing agent. The solubilizing agent or a mixture of solubilizing agents is chosen from the group consisting of a surfactant, such as, for example, polysorbate 80 (Tween 80) and the like, a complexing agent, such as, for example, beta-cyclodextrins and the like, a polymer, such as, for example, poloxamer 188, and the like, a co-solvent, such as, for example, methanol and the like.

The solution is filled into vials, stoppered and frozen at about −40° C. Lyophilization was started at a shelf temperature of about −15° C. for about 22 hours under a vacuum of about 150 mTorr, followed by drying at about 40° C. for about 12 hours to afford amorphous atorvastatin.

In the third aspect of the present invention, atorvastatin is dissolved in a hydroxylic solvent, such as, for example, water containing an alkalizing agent, such as, for example, an alkali metal salt, for example, a sodium phosphate and the like, an alkali metal hydroxide, for example, sodium hydroxide and the like, an alkaline earth metal salt, for example, calcium phosphate and the like, or an amino acid, for example, lysine and the like, or a volatile base, for example, ammonium hydroxide, a tetraalkylammonium hydroxide, for example, tetrabutylammonium hydroxide and the like, a secondary amine, for example, diethanolamine and the like, a tertiary amine, for example, triethanolamine and the like, and an aryl amine, for example, benzalkonium chloride and the like.

The solution was filtered and filled into flat bottom glass dishes which are loaded into a freeze-dryer and the solution frozen to a shelf temperature of about −40° C. Lyophilization was started at a shelf temperature of about −15° C. for about 93 hours under a vacuum of about 150 m Torr. The resulting amorphous atorvastatin was dried at about 40° C. for about 12 hours.

Preferably, the alkalizing agent is an aluminum salt, a magnesium salt, a calcium salt, monoethanolamine, diethanolamine, or a sodium phosphate.

In the fourth aspect of the present invention, atorvastatin is dissolved in a hydroxylic solvent, such as, for example, water containing a pharmaceutically acceptable antioxidant such as, for example, a chelating agent, for example, citrate, ethylenediaminotetraacetic acid (EDTA) and the like, a free radical scavenger, for example, butylated hydroxyanisole (BHA), butylated hydroxytoluene, alpha-tocopherol and the like, or an oxygen scavenger, for example, sodium ascorbate, potassium ascorbate and the like. The solution is frozen and lyophilized as described previously in the first aspect of the present invention.

Preferably, the antioxidant is BHA and the solvent is water.

Other features and embodiments of the invention will become apparent from the following examples which are given for illustration rather than for limiting its intended scope.

EXAMPLE 1

Preparation of Amorphous Atorvastatin Calcium by Freeze-Drying from a Solution of Dimethyl Sulfoxide Method A Crystalline atorvastatin calcium (U.S. Pat. No. 5,969,156), 101.2 mg, was dissolved by shaking in 3 ml of dimethylsulfoxide (DMSO). The solution was diluted to 5 ml by the addition of DMSO and filtered through a 25 mm 0.22 μm syringe tip filter into a 5 ml Flint type I tubular glass vial. The unstoppered vial was loaded into a freeze-dryer (Virtis Advantage EL, Gardiner, N.Y.) and the solution was frozen at a shelf temperature of −40° C. Lyophilization was started at a shelf temperature of −24° C. followed by drying at a shelf temperature of 0° C. and then 5° C. Pressure was below 50 m Torr during the drying cycle. Additionally, the atorvastatin calcium was dried at 40° C. for 6 hours under vacuum in a vacuum oven.

The lyophilized sample was analyzed by XRD and $^{19}$F SS NMR. The powder XRD diffraction pattern showed a very broad peak from approximately 15-30 2θ that is typical of amorphous solids (FIG. 1).

Figure 2:
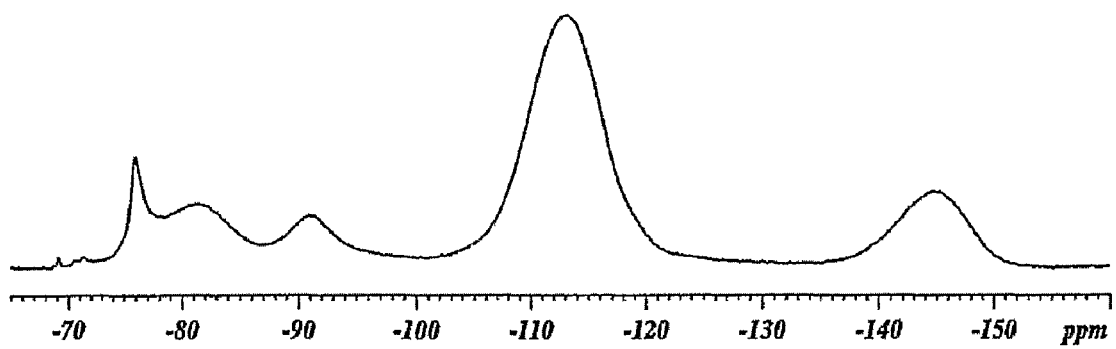
FIG. 2 shows a solid-state $^{19}$F nuclear magnetic resonance (NMR) spectrum of amorphous atorvastatin calcium made in Example 1, Method A.

The solid state $^{19}$F SS NMR spectrum is shown in FIG. 2. The spectrum has a broad peak at δ of approximately 113 ppm indicating that it is amorphous atorvastatin calcium. The two broad peaks at approximately 91 and 145 ppm are side spinning bands.

Method B

Crystalline atorvastatin calcium (U.S. Pat. No. 5,696,156) 1.0066 g. was dissolved by shaking in 7 ml of DMSO. The solution was diluted to 10 ml by the addition of DMSO and filtered through a 25 mm 0.22 μm syringe tip filter into two 5 ml Flint type I tubular glass vials. Each vial which contained approximately 5 ml of solution was lyophilized as described in Method A.

Figure 3:
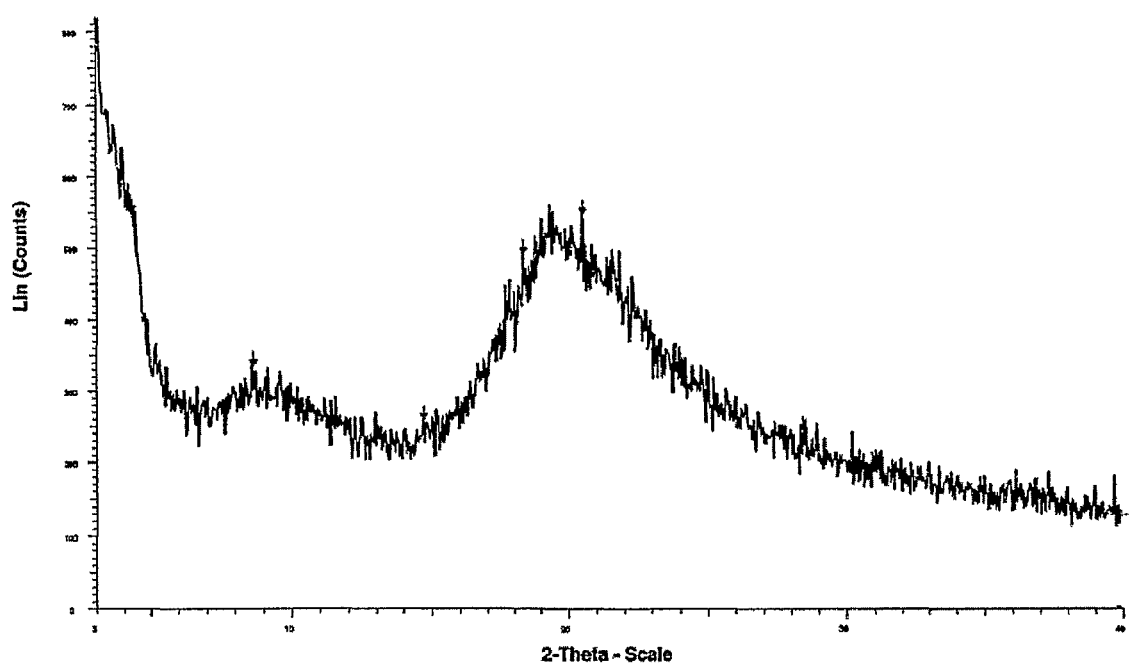
FIG. 3 shows a powder x-ray diffraction (XRD) diffractogram of amorphous calcium made in Example 1, Method B.

The lyophilized sample was analyzed by XRD and $^{19}$F SS NMR. The XRD diffraction pattern showed a very broad peak from approximately 15-30 2θ that is typical of amorphous solids (FIG. 3).

Figure 4:
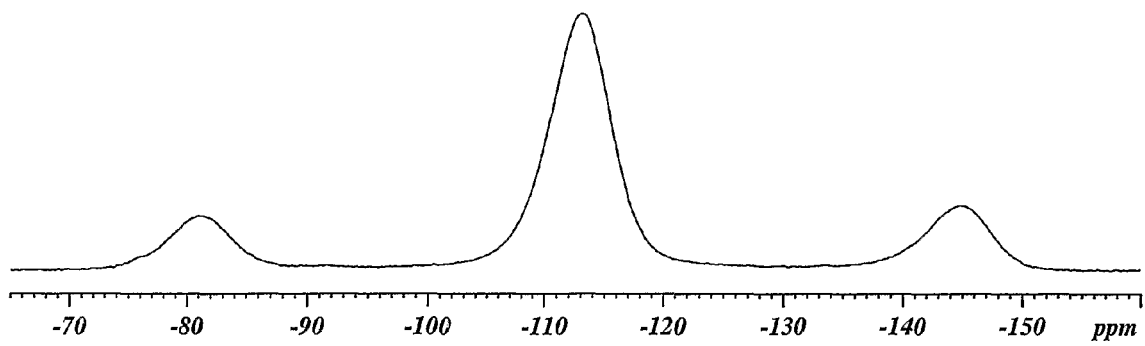
FIG. 4 shows a solid state $^{19}$F nuclear magnetic resonance (NMR) spectrum of amorphous atorvsatatin calcium made in Example 1, Method B.

The solid state $^{19}$F SSNMR spectrum is shown in FIG. 4. The spectrum has a broad peak at δ of approximately 113 ppm indicating that it is amorphous atorvastatin calcium. The two broad peaks at approximately 81 and 145 ppm are side spinning bands.

EXAMPLE 2

Preparation of Amorphous Atorvastatin Calcium by Freeze-Drying from an Aqueous Solution Containing a Solubilizing Agent Method A Crystalline atorvastatin calcium (U.S. Pat. No. 5,969,156), 200.1 mg, was dissolved in approximately 70 ml of Dulbecco's phosphate buffered saline solution (PBS) containing 5.03 g of Tween 80. The solution was diluted to 100 ml with PBS and the final concentration of the solution contained 2 mg/ml of atorvastatin calcium. Two ml of solution was volumetrically filled into 20 ml Flint Type I tubular glass vials in a laminar flow hood. Stoppers (20 mm Lyophile D777-1, B2TR Fluoro Single Vent) were partially inserted into the vials. The vials were lyophilized using a Virtis Genesis 25 EL freeze-dryer (Gardiner, N.Y.) using the following cycle: samples were frozen at −40° C. followed by vacuum drying at a shelf temperature of −15° C. for approximately 22 hours under vacuum of 150 m Torr followed by drying at 40° C. for approximately 12 hours. The lyophilizer chamber was back filled with nitrogen. Amorphous atorvastatin calcium is produced.

Method B

Beta-Cyclodextrin is dissolved in an appropriate amount of water for injection (WFI) to afford a 20% w/w concentration. Crystalline atorvastatin calcium (U.S. Pat. No. 5,969,156) is added to the solution and the final concentration of the solution contained 10 mg/ml of atorvastatin calcium. The solution is lyophilized as described in Method A to afford a lyophilized cake which contains amorphous atorvastatin calcium.

EXAMPLE 3

Preparation of Amorphous Atorvastatin Calcium by Freeze-Drying from a Solution Containing a Pharmaceutically Acceptable Alkalizing Agent or a Buffer Method A Crystalline atorvastatin calcium (U.S. Pat. No. 5,969,156), 100.5 mg, was dissolved in approximately 700 ml of deionized water and the pH adjusted to 8.53 by the addition of solutions of NaOH and HCl. The solution was diluted to 1000 ml with deionized water. The solution was filtered through a 0.22 μm GV Durapore Stericup and filled at approximately 333 ml into 3 large flat bottom glass dishes. The dishes were loaded into a freeze dryer (Virtis Genesis 25 EL, Gardiner, N.Y.) and lyophilized according to the following cycle: samples were frozen at −40° C. followed by vacuum drying at a shelf temperature of −15° C. for approximately 93 hours, under vacuum at 150 m Torr, followed by drying at 40° C. for approximately 12 hours.

The resulting dried product was collected and analyzed by $^{19}$F solid state NMR.

Figure 5:
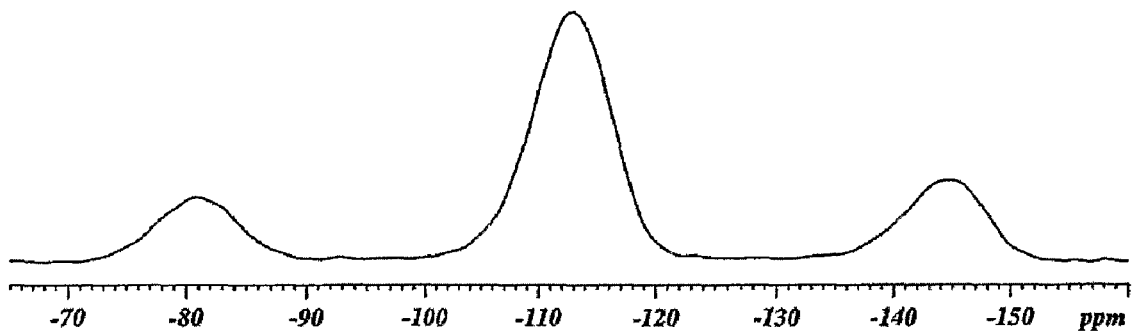
FIG. 5 shows a solid state $^{19}$F nuclear magnetic resonance (NMR) spectrum of amorphous atorvastatin calcium made in Example 3, Method A.

The solid state $^{19}$F NMR spectrum is shown in FIG. 5. The spectrum has a broad peak at δ at approximately 113 ppm indicating that it contains amorphous atorvastatin calcium.

Method B

Crystalline atorvastatin calcium (U.S. Pat. No. 5,969,156), 1 g, and 0.1 g of sodium phosphate are mixed in 100 ml of DMSO. The solution is freeze-dried as described in Example 1 to afford lyophilized amorphous atorvastatin calcium.

EXAMPLE 4

Preparation of Amorphous Atorvastatin Calcium by Freeze-Drying from a Solution Containing a Pharmaceutically Acceptable Antioxidant Beta-Cyclodextrin is dissolved in an appropriate amount of water for injection (WFI) to afford a 20% w/w concentration. Crystalline atorvastatin calcium (U.S. Pat. No. 5,969,156) is added to the solution and the final concentration of the solution contained 10 mg/ml of atorvastatin calcium. Butylated hydroxanisole (BHA) is dissolved to achieve a concentration of 0.02%. The solution is lyophilized as described in Example 2, Method A to afford a lyophilized cake which contains amorphous atorvastatin calcium.

EXAMPLE 5

Milling of the Freeze-Dried Amorphous Atorvastatin Calcium

Freeze-dried amorphous atorvastatin calcium is milled using one of the common pharmaceutical methods known in the art (e.g., using a ball mill) in order to obtain a desired particle size distribution. The milled material can be further processed by, e.g., wet granulation or dry granulation and used to manufacture a solid dosage form.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A process for forming amorphous atorvastatin comprising:
   (a) dissolving atorvastatin in a water solvent with a solubilizing agent selected from a group consisting of: a polyoxyethylene fatty acid ester and a cyclodextrin; and
   (b) lyophilizing the solution to afford said amorphous atorvastatin.

2. The process of claim 1 wherein the solubilizing agent is selected from the group consisting of polysorbate 80 and a cyclodextrin.

3. The process of claim 2 wherein the cyclodextrin is beta-cyclodextrin.

* * * * *